US008353871B2

(12) United States Patent
Zimmerman et al.

(10) Patent No.: US 8,353,871 B2
(45) Date of Patent: Jan. 15, 2013

(54) DRUG DELIVERY DEVICE WITH NEEDLES AND ROLLER

(75) Inventors: Yotam Zimmerman, Hadera (IL); Amir Waldman, Yarqona (IL)

(73) Assignee: Roller Jet Ltd., Yarkona (IL)

( * ) Notice: Subject to any disclaimer, the term of this patent is extended or adjusted under 35 U.S.C. 154(b) by 192 days.

(21) Appl. No.: 12/830,356

(22) Filed: Jul. 5, 2010

(65) Prior Publication Data
US 2012/0004638 A1  Jan. 5, 2012

(51) Int. Cl.
*A61M 5/00* (2006.01)
*A61M 5/178* (2006.01)
*A61H 7/00* (2006.01)
*A61H 19/00* (2006.01)

(52) U.S. Cl. ........... 604/116; 604/179; 604/158; 601/99

(58) Field of Classification Search .......... 604/272–274, 604/156, 158, 115–117, 15–21, 52, 63, 99, 604/102; 606/32, 34
See application file for complete search history.

(56) References Cited

U.S. PATENT DOCUMENTS

| 1,688,332 | A | * | 10/1928 | Heck, Jr. et al. | 604/156 |
| 3,918,449 | A | * | 11/1975 | Pistor | 604/47 |
| 6,766,192 | B1 | * | 7/2004 | D'Africa et al. | 604/20 |
| 7,166,086 | B2 | | 1/2007 | Haider et al. | |
| 2006/0051404 | A1 | * | 3/2006 | Yeshurun et al. | 424/449 |
| 2006/0206062 | A1 | * | 9/2006 | Naimark et al. | 604/264 |
| 2007/0073217 | A1 | | 3/2007 | James | |

FOREIGN PATENT DOCUMENTS

| DE | 2319591 | 11/1974 |
| WO | 2004/045671 | 6/2004 |

OTHER PUBLICATIONS

PCT Search Report PCT/US2011/042912.

* cited by examiner

*Primary Examiner* — Nicholas Lucchesi
*Assistant Examiner* — Rebecca E Eisenberg
(74) *Attorney, Agent, or Firm* — Dekel Patent Ltd; David Klein

(57) ABSTRACT

A delivery device including a roller rotatably mounted on an axle, a reservoir, and at least one hollow needle positioned in the roller are in fluid communication with the reservoir, wherein as the roller rotates about the axle, contents of the reservoir pass through the at least one hollow needle.

9 Claims, 2 Drawing Sheets

DRUG DELIVERY DEVICE WITH NEEDLES AND ROLLER

FIELD OF THE INVENTION

The present invention generally relates to drug delivery through the skin, such as for skin treatment and rejuvenation, but also for delivery of drugs such as insulin and others.

BACKGROUND OF THE INVENTION

Punctile resurfacing has been developed for effective skin rejuvenation for the improvement of moderate wrinkles, scars, pores, pigmentation and skin texture. Pin point, segmental or fractional injuries to the epidermis can be delivered by needles.

For example, the MEDICAL ROLL CIT system, commercially available from VIVIDA SA of South Africa, employs a hand held roller with widely spaced micro-needles. The micro-needles only penetrate through the epidermis but do not remove or ablate it. This causes minute damages to the epidermis and percutaneous induces generation of collagen as a natural response to the wounds. After creating the micropunctures in the epidermis, skin care substances are introduced by applying a lotion or cream over the wounded area. The active ingredients in the skin care substances pass through the micro-holes and thus are substantially more effective than topically applied drugs on the stratum corneum.

Another example is described in US Patent Application 20070073217 to James (published Mar. 29, 2007), which is a device for delivering a bioactive material to a subterranean layer of skin. The device has a roller head with needles that are operable to penetrate the stratum corneum. A bioactive material is disposed on one or more of the needles, whereby movement of the head operates to pick up the bioactive material and to deliver a portion of the bioactive material to a selected location, the selected location being a dermis, or an epidermis, or both the dermis and the epidermis. The bioactive material is, for example, a protein, a vitamin, a gene, a growth agent, a drug, and a peptide. The needles create an injury that triggers collagen production from one or more fibroblasts in the skin.

Multiple micro-needles have also been suggested for drug delivery, such as vaccines, through the skin. For example, U.S. Pat. No. 7,166,086 to Haider et al. (granted Jan. 23, 2007) describes a device for the delivery of a substance into skin via the rotational movement of a microabrader device. A substance is applied to the skin through the rotational movement of microprotrusions which may be imparted by a spring device present in the microabrader device or the motion of the operator through the handle of the microabrader device. The device can monitor its pressure against the skin. The delivered substance may be placed on the microprotrusions and a reconstituting liquid included in the microabrader device.

It is noted that Haider et al. distinguishes between different modes of delivering a drug through the stratum corneum, and this distinction is used in the description and claims of the present invention as well. The term "abrade" refers to removing at least a portion of the stratum corneum to increase the permeability of the skin without causing excessive skin irritation or compromising the skin's barrier to infectious agents. This is in contrast to "puncturing" which produces discrete holes through the stratum corneum with areas of undisrupted stratum corneum between the holes. The term "penetrating" refers to entering the stratum corneum without passing completely through the stratum corneum and entering into the adjacent layers. This is not to say that that the stratum corneum cannot be completely penetrated to reveal the interface of the underlying layer of the skin. "Piercing", on the other hand, refers to passing through the stratum corneum completely and entering into the adjacent layers below the stratum corneum. It is noted that Haider et al. explicitly states that its device is for abrading the stratum corneum and not for puncturing.

SUMMARY OF THE INVENTION

The present invention seeks to provide improved apparatus for drug delivery through the skin, such as for skin treatment and rejuvenation and for delivering drugs such as insulin. The apparatus includes a roller with hollow needles and a drug reservoir for delivering the drug through the needles as the roller is passed over the skin, as is described more in detail hereinbelow. The terms drug, substance and medicament are used interchangeably throughout the description and claims.

There is thus provided in accordance with an embodiment of the present invention a delivery device including a roller rotatably mounted on an axle, a reservoir, and at least one hollow needle positioned in the roller are in fluid communication with the reservoir, wherein as the roller rotates about the axle, contents of the reservoir pass through the at least one hollow needle.

In accordance with an embodiment of the present invention a piston is arranged with respect to the roller such that there is relative sliding motion between the roller and the piston as the roller rotates about the axle, the relative sliding motion causing the piston to push contents of the reservoir through the at least one needle.

In accordance with an embodiment of the present invention the axle is in threaded connection with the roller and the roller moves axially along the axle as the roller rotates about the axle.

In accordance with an embodiment of the present invention the at least one hollow needle is in fluid communication with the reservoir via a conduit, and the roller rotates with respect to the conduit. For example, the needle may be in fluid communication with the reservoir via the conduit at a first rotational orientation of the roller with respect to the conduit, whereas at a second rotational orientation of the roller with respect to the conduit it is not in fluid communication with the reservoir.

In accordance with an embodiment of the present invention the conduit is formed in a conduit member, and there is at least one guide pin that extends from the conduit member and slides in at least one aperture formed in the piston.

In accordance with an embodiment of the present invention a handle is provided for grasping by a user, the roller being rotatably connected to the handle.

There is also provided in accordance with an embodiment of the present invention a method for puncturing skin including placing the device of the invention on the skin, and rotating the roller along the skin, wherein as the roller rotates, the at least one hollow needle punctures the skin and contents of the reservoir pass through the at least one hollow needle into the skin.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1:
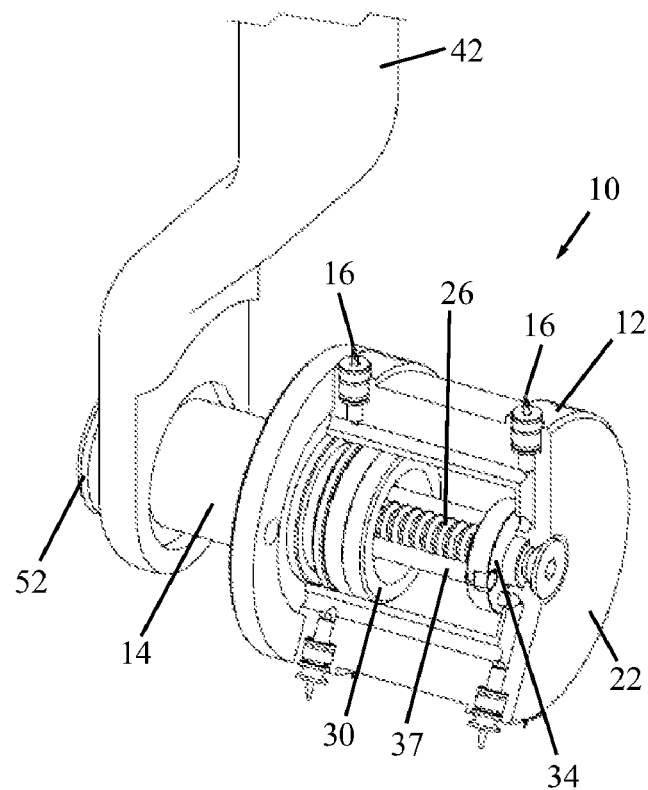
FIG. 1 is a simplified pictorial, partially cutaway illustration of a drug delivery device, constructed and operative in accordance with an embodiment of the present invention.
Figure 2:
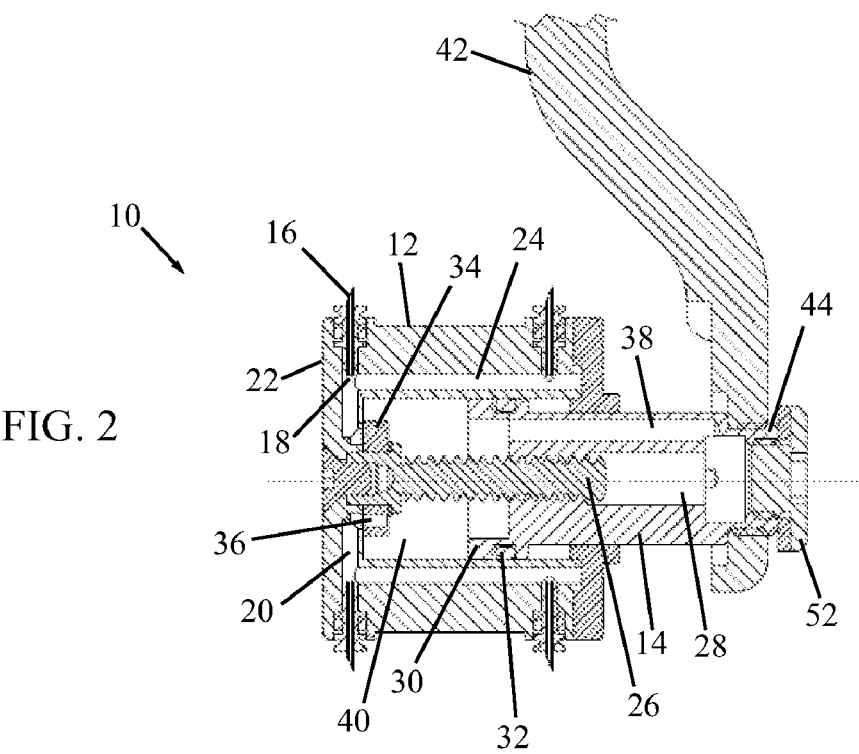
FIGS. 2 and 3 are simplified sectional illustrations of the drug delivery device of FIG. 1, respectively showing a drug reservoir in the device in full and empty configurations.
Figure 3:
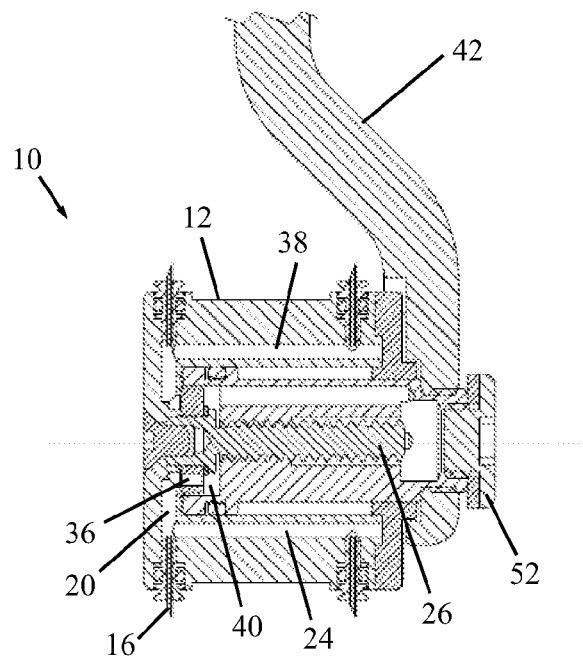

Reference is now made to FIGS. 1-3, which illustrate a drug delivery device 10, constructed and operative in accordance with a non-limiting embodiment of the present invention.

Device 10 includes a roller 12 rotatably mounted on an axle 14. One or more hollow needles 16 protrude radially outwards from the outer contour of the roller 12. In the illustrated embodiment, there are two or more sets of needles axially spaced from one another, each set of needles including a plurality of needles radially spaced from each other. A proximal end 18 of each needle 16 (i.e., the end opposite the tip of the needle) fluidly communicates with a radial channel 20, formed radially inwards at a distal end 22 of the roller 12. The set of needles 16 that are close to distal end 22 communicate directly with radial channel 20. The other set of needles communicate with radial channel 20 via axial channels 24.

The distal end 22 of roller 12 is connected to a threaded shaft 26, which in turn is threadedly connected with an internally-threaded bore 28 formed in axle 14. A distal end of axle 14 forms a piston 30 that faces the internal face of the distal end 22 of roller 12. The movement of roller 12 relative to piston 30 is sealed by an O-ring 32.

The distal end of threaded shaft 26 passes through a (round) conduit member 34 (and serves as a bearing for member 34), adjacent the internal face of the distal end 22 of roller 12. A conduit 36 is formed at the lower end of conduit member 34 (lower in the sense of the drawings). One or more guide pins 37 (seen in FIG. 1 and not seen in FIGS. 2-3) extend from conduit member 34 and slide in apertures (not seen) formed in piston 30. One or more apertures 38 (FIGS. 2-3) are formed in piston 30 and serve for refilling, as will be described further below.

A reservoir 40 is formed in the volume bounded by the distal end of piston 30, inner walls of roller 12 and internal face of the distal end 22 of roller 12. A substance to be delivered to a subject is stored in reservoir 40.

A handle 42 is provided for grasping by a user. Handle 42 may be fixed to axle 14, such as by a threaded connection 44 or any other suitable connection (e.g., welding). Roller 12 thus rotates relative to axle 14 and handle 42.

To use the device 10, the user grasps handle 42 and places device 10 on skin to be punctured. The user then rolls the device 10 along on the skin, causing roller 12 to rotate about axle 14. As roller 12 rotates about axle 14, simultaneously there is relative sliding motion between roller 12 and piston 30. Specifically, in the non-limiting illustrated embodiment, as roller 12 rotates, threaded shaft 26 screws into internally-threaded bore 28 and the internal face of the distal end 22 of roller 12 advances axially towards piston 30. The axial movement is guided by guide pins 37 to form constant orientation between axial channels 24 and handle 42 (and axle 14 that is connected to handle 42). The axial movement causes piston 30 to push the contents of reservoir 40 through conduit 36. As seen in FIG. 3, the contents flowing through conduit 36 can continue to flow to needles 16 only when radial channel 20 is aligned with conduit 36. In this manner, the substance is constrained to flow only through the lower needles which are the needles which puncture the skin. Accordingly, as roller 12 rotates along the skin, the hollow needles 16 puncture the skin and contents of the reservoir 40 pass through the needles 16 into the skin.

In this embodiment, the needles 16 are in fluid communication with reservoir 40 via conduit 36 at a first rotational orientation of roller 12 with respect to conduit 36 (when the lower radial channel 20 is aligned with conduit 36), whereas at a second rotational orientation there is no fluid communication with reservoir 40 (the upper radial channels are blocked). Alternatively, all of the needles could be in fluid communication with the reservoir during the full rotation of the roller, if desired.

In the prior art devices mentioned above, the substance is either applied after abrasion or pricking, or is applied over the abrading elements. In contrast, in the present invention, the substance passes directly through the hollow needles as they puncture the skin. This is a much more effective way of delivering the substance through the skin.

Figure 4:
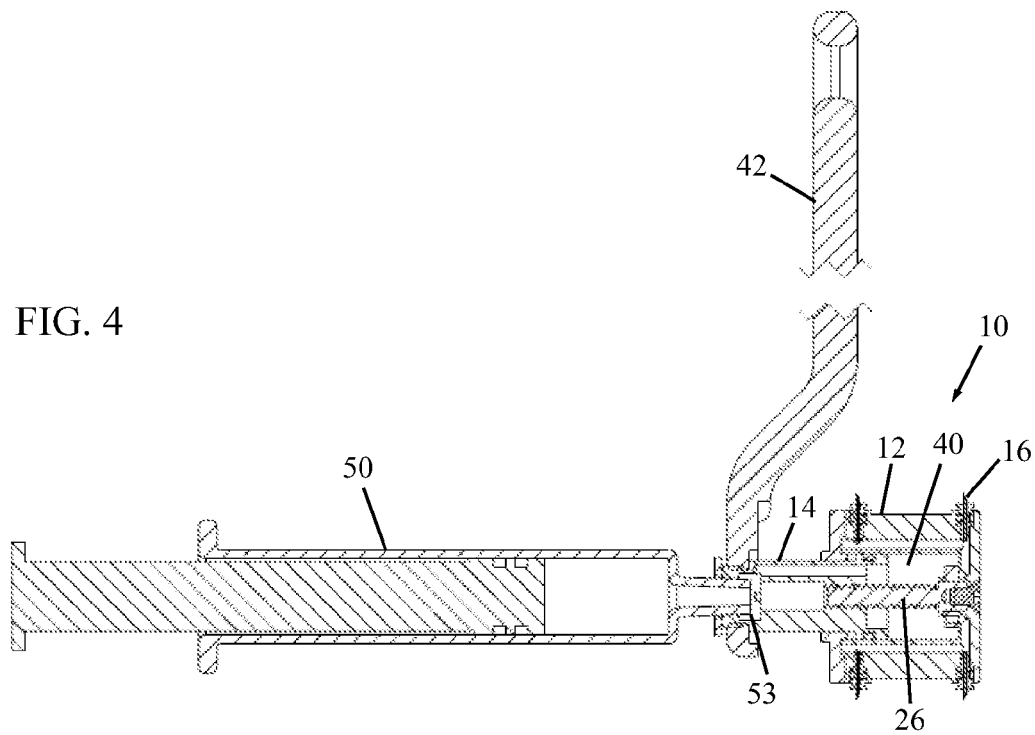
FIG. 4 is a simplified sectional illustration of filling the drug delivery device with a syringe, in accordance with an embodiment of the present invention.

Reference is now made to FIG. 4, which illustrates filling drug delivery device 10 with a syringe 50, in accordance with an embodiment of the present invention. Drug delivery device 10 may include a septum 52 (seen in FIGS. 1-3) at the junction of handle 42 with roller 12. The needle (not shown) of syringe 50 may puncture septum 52 to introduce a substance into reservoir 40, wherein after withdrawing the needle, septum 52 fluidly seals reservoir 40. Alternatively, as shown in FIG. 4, septum 52 may be removed, in which case syringe 50 injects the substance into reservoir 40 via an adapter 53, and septum 52 is then put back in place to seal reservoir 40.

It is noted that the substance may fill the volume of reservoir 40 by flowing through apertures 38. In such a case, the volume of reservoir 40 is not just bounded by the distal end of piston 30, inner walls of roller 12 and internal face of the distal end 22 of roller 12, but also includes the volume available for flow through apertures 38 to the inner face of septum 52.

It is noted that in one of the options of the invention, the device can be single use, and may include the injectable material in it (provided with a full syringe).

The scope of the present invention includes both combinations and subcombinations of the features described hereinabove as well as modifications and variations thereof which would occur to a person of skill in the art upon reading the foregoing description and which are not in the prior art.

What is claimed is:

1. A delivery device comprising:
   a roller rotatably mounted on an axle;
   a reservoir; and
   at least one hollow needle positioned in said roller are in fluid communication with said reservoir, wherein as said roller rotates about said axle, contents of said reservoir pass through said at least one hollow needle; and
   a piston arranged with resect to said roller such that there is relative sliding motion between said roller and said piston as said roller rotates about said axle, said relative sliding motion causing said piston to push contents of said reservoir through said at least one needle, and wherein said piston does not slide perpendicular to said axle of said roller.

2. The delivery device according to claim 1, wherein said axle is in threaded connection with said roller and said roller moves axially along said axle as said roller rotates about said axle.

3. The delivery device according to claim 1, wherein said at least one hollow needle is in fluid communication with said reservoir via a conduit, and said roller rotates with respect to said conduit.

4. The delivery device according to claim 3, wherein said at least one hollow needle is in fluid communication with said reservoir via said conduit at a first rotational orientation of said roller with respect to said conduit, and is not in fluid communication with said reservoir at a second rotational orientation of said roller with respect to said conduit.

5. The delivery device according to claim 1, further comprising at least one guide pin that slides in at least one aperture formed in said piston.

6. The delivery device according to claim 1, further comprising a handle for grasping by a user, said roller being rotatably connected to said handle.

7. The delivery device according to claim 1, further comprising a septum that fluidly seals said reservoir.

8. A method for puncturing skin comprising:
 placing the device of claim 1 on skin; and
 rotating said roller along the skin, wherein as said roller rotates, said at least one hollow needle punctures the skin and contents of said reservoir pass through said at least one hollow needle into the skin.

9. A delivery device comprising:
 a roller rotatably mounted on an axle;
 a reservoir; and
 at least one hollow needled positioned in said roller are in fluid communication with said reservoir, wherein as said roller rotates about said axle, contents of said reservoir pass through said at least one hollow needle; and
 a piston arranged with respect to said roller such that there is relative sliding motion between said roller and said piston as said roller rotates about said axle, said relative sliding motion causing said piston to push contents of said reservoir through said at least one needle, and wherein said at least one hollow needle is in fluid communication with said reservoir via a conduit formed in a conduit member, said roller rotating with respect to said conduit, and further comprising at least one guide pin that extends from said conduit member and slides in at least one aperture formed in said piston.

* * * * *